(12) United States Patent
Maunoury

(10) Patent No.: US 8,987,472 B2
(45) Date of Patent: Mar. 24, 2015

(54) N-CYCLOALKYLALKYL TRISCARBAZOLES

(75) Inventor: Jonathan Maunoury, Brussels (BE)

(73) Assignee: Solvay SA, Brussels (BE)

( * ) Notice: Subject to any disclaimer, the term of this patent is extended or adjusted under 35 U.S.C. 154(b) by 7 days.

(21) Appl. No.: 13/878,415

(22) PCT Filed: Oct. 7, 2011

(86) PCT No.: PCT/EP2011/005015
§ 371 (c)(1),
(2), (4) Date: Aug. 28, 2013

(87) PCT Pub. No.: WO2012/048821
PCT Pub. Date: Apr. 19, 2012

(65) Prior Publication Data
US 2013/0331582 A1 Dec. 12, 2013

(30) Foreign Application Priority Data
Oct. 11, 2010 (EP) .................... 10187128

(51) Int. Cl.
*C07D 209/88* (2006.01)
*C07D 209/86* (2006.01)
*H01L 51/00* (2006.01)

(52) U.S. Cl.
CPC .......... *H01L 51/0072* (2013.01); *C07D 209/88* (2013.01)
USPC ..................... 548/440

(58) Field of Classification Search
CPC ............ C07D 209/88; C07D 209/86
See application file for complete search history.

(56) References Cited

U.S. PATENT DOCUMENTS

| | | | |
|---|---|---|---|
| 7,504,162 B2 * | 3/2009 | Nomura et al. | 428/690 |
| 8,546,505 B2 * | 10/2013 | Zhang et al. | 526/259 |
| 8,586,973 B2 * | 11/2013 | Martin et al. | 257/40 |
| 2005/0031899 A1 * | 2/2005 | Nomura et al. | 428/690 |
| 2012/0168732 A1 * | 7/2012 | Zhang et al. | 257/40 |
| 2012/0172556 A1 * | 7/2012 | Zhang et al. | 526/259 |
| 2014/0001449 A1 * | 1/2014 | Maunoury et al. | 257/40 |

FOREIGN PATENT DOCUMENTS

| | | |
|---|---|---|
| WO | WO-2004/101517 | 11/2004 |
| WO | WO-2009/080799 | 7/2009 |
| WO | WO 2011057706 A2 * | 5/2011 |

OTHER PUBLICATIONS

Yang et al. Chem. Commun., 2010, 46, 1088-1090.*
Radecki et al., Analytical Sciences (2004) vol. 20, 1599-1603.*
Xing et al Sensors and Actuators B 114 (2006) 28-31.*
McClenaghan et al. JACS (2003), 125, 5356-5365.*
Hameurlaine et al. Tetrahedron Letters 44 (2003) 957-959.*
Knights et al. Journal of Material Chemistry, vol. 18 (2008), pp. 2121-2130.*

* cited by examiner

*Primary Examiner* — Nyeemah A Grazier

(57) ABSTRACT

The present invention relates to a novel triscarbazole compound comprising cyclo- or polycycloalkyl or aralkyl substituent, which can be represented by Formula (I).

Formula (I)

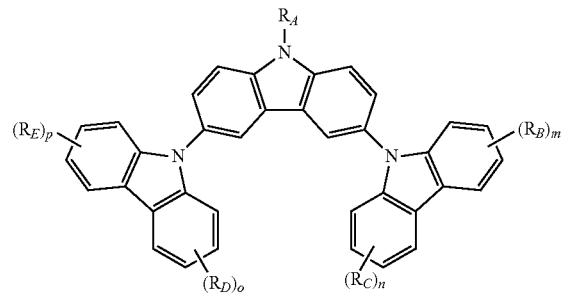

wherein;

$R_A$ is a substituent comprising a substituted or unsubstituted cyclo- or polycycloalkyl group wherein the ring system comprises three to twenty carbon atoms or an aralkyl group having an overall number of nine to twenty carbon atoms, $R_B$, $R_C$, $R_D$ and $R_E$ are any substituent other than a substituted or unsubstituted aniline, and m, o, p and q are same or different at each occurrence and represent an integer from 0 to 4.

11 Claims, 2 Drawing Sheets

| Cs₂CO₃/Al |
|---|
| 3TPYMB(30nm) |
| TCz2:tBuOXD-7:Firpic (70nm) |
| CH8000 (60nm) |
| ITO / Glass |

FIG. 3

N-CYCLOALKYLALKYL TRISCARBAZOLES

The present invention relates to a novel triscarbazole compounds comprising cyclo- or polycycloalkyl or aralkyl substituents and an organic device comprising at least one layer containing the compounds according to the present invention.

BACKGROUND ART

Recently, various devices have been under active study and development, particularly those based on electroluminescence (EL) from organic materials.

The use of phosphorescent materials has been a major breakthrough in boosting electroluminescence efficiency since they allow simultaneous harvesting of both singlet and triplet excitons.

Unfortunately, the emission lifetimes of these phosphorescent complexes are relatively long, leading to undesired triplet-triplet annihilation during the operation of a device. To overcome this problem, phosphorescent emitters are doped into organic host materials.

Selecting a suitable host material for phosphorescent dopants remains one of the critical issues in phosphorescence-based OLEDs.

An ideal host material would meet the following intrinsic requirements: a triplet energy gap (Et) larger than that of the triplet dopant to prevent reverse energy transfer from the guest back to the host, good carrier transporting properties to balance the charge flux and reduce the driving voltage, thermal and morphological stability to extend the device operational lifetime.

Well-known host materials for guest-host systems include hole-transporting 4,4'-N,N'-dicarbazolyl-biphenyl (CBP) and electron-transporting aluminum 8-hydroxyquinoline ($Alq_3$), which have been used in OLEDs. Those host materials have suitable properties for green and red emitters.

In contrast, highly efficient blue-light emitting phosphorescent devices remain rare, mainly because of the lack of suitable host materials possessing both charge transporting characteristics and high triplet energy.

Several host materials for better phosphorescent emission have been reported. Due to their charge conducting ability, photophysical and redox properties, sufficiently large triplet energies and carrier-transport properties, carbazole-based compounds have been actively studied.

For example, U.S. Patent Application Publication No. US 2003/205696 discloses guest-host emissive systems suitable for use with organic light emitting devices in which the host material comprises a compound having a carbazole core with an electron-donating species bonded to nitrogen, aromatic amine groups or carbazole groups bonded to one or more of the carbon atoms, a large band gap potential, and high-energy triplet excited states. Such materials permit short-wavelength phosphorescent emission by an associated guest material, and the combination of said materials with emissive phosphorescent organometallic compounds such as iridium complexes is useful in the fabrication of organic light emitting devices.

U.S. Patent Application Publication No. US 2005/0031899 discloses carbazole derivatives used as an organic semiconductor element, a light emitting element and an electronic device by employing the carbazole derivative. N-benzyl-3,6-di-(N-carbazolyl)carbazole is used as starting material for the preparation of 3,6-di-(N-carbazolyl)carbazole in synthesis example 4.

U.S. Patent Application Publication No. US 2009/080799 discloses norbornene-monomer, poly(norbornene) homopolymer, and poly(norbornene) copolymer compounds containing a functionalized carbazole side chain used as hole transport and/or electron blocking materials and as organic host materials for an organic luminescence layer and an OLED device.

Further, Lengvinaite et al., "Carbazole-based aromatic amines having oxetanyl groups as materials for hole transporting layers," Synthetic Metals, 157: 529-533 (2007), discloses several oxetane-functionalized carbazole-based aromatic amines.

Tsai et al., "3-(9-carbazolyl)carbazoles and 3,6-di(9-carbazolyl)carbazoles as effective host materials for efficient blue organic electrophosphorescence," Adv. Mater., 19: 862-866 (2007), and Tsai et al., "P-152: Efficient blue phosphorescent OLEDs employing novel oligocarbazoles as high-triplet-energy host materials," SID 07 DIGEST, 38(Bk. 1): 772-775 (2007), disclose a strong dependence of the linking topology on the electronic coupling between monomeric carbazole units for directly linked oligocarbazoles.

Knights et al., "A rapid route to carbazole containing dendrons and phosphorescent dendrimers", J. Mater. Chem. 2008, 18, 2121-2130, discloses N-benzyl-3,6-di(N-Carbazolyl)carbazole, wherein the carbazole substituents in 3 and 6 position are substituted themselves by fluorene substitutents.

Radecki et al., "Oligocarbazoles as ligands for lead-selective liquid membrane electrodes", Analyt. Sci., November 2004, Vol. 20, 1599-1603 discloses N-benzyl-3,6-di(N-(3',6'-di-tert.butyl)carbazolyl)carbazole as ionophore in liquid membrane electrodes for lead determination in water samples.

Hameurlaine et al., "Synthesis of soluble oligocarbazole derivatives, Tetrahedron Letters, Vol. 44 No. 5, 2003, 957, also discloses N-benzyl-3,6-di(N-(3',6'-di-tert.butyl)carbazolyl)carbazole as a building block in the synthesis of trimeric and heptameric carbazoles with good solubilities in organic solvents.

It is described in the above literatures that 3(6), 9'-linked oligocarbazoles investigated exhibit fairly high thermal stability. By adjusting the thickness of the hole-transport layer in the OLED device comprising the alkyl chain substituted triscarbazole (e.g., 2-ethylhexyl triscarbazole), lower operating voltages and higher power efficiencies were observed. However, none of the above-disclosed materials meets all the requirements necessary for OLED application, e.g., suitable energy level, charge transport ability, processibility from a solution with uniform film formation, ability to form an amorphous phase, ability for good dopant dispersion, morphological stability (high Tg), and thermal and electrochemical stabilities under operational conditions of the device. For example, substitution of branched alkyl chain on triscarbazoles (e.g., 2-ethylhexyl triscarbazole) increases the solubility in organic solvent but decreases the glass transition temperature (Tg) to thereby make the material difficult to sublimate while lowering the stability of glassy film morphology in the device leading to degraded lifetime. Tsai et al. also mention in the above literatures that for the same oligomer length, substitution by rigid and bulkier groups gives higher Tg values than alkyl substitution, and high Tg values for these new host materials are also expected to benefit the stability of the devices.

Thus, there has been a need to develop new host materials, which are capable of satisfying all of the requirements indicated above.

SUMMARY OF INVENTION

It has been found that when cyclo- or polycycloalkyl or aralkyl substituents in accordance with the present invention are introduced into the triscarbazole compound instead of alkyl substituents, Tg is raised while maintaining solubility without any adverse effects on the other properties.

The present invention accordingly provides triscarbazole compounds comprising a substituted or unsubstituted cyclo- or polycycloalkyl or aralkyl substituent. Specifically, the triscarbazole compounds of the present invention are characterized by formula (I):

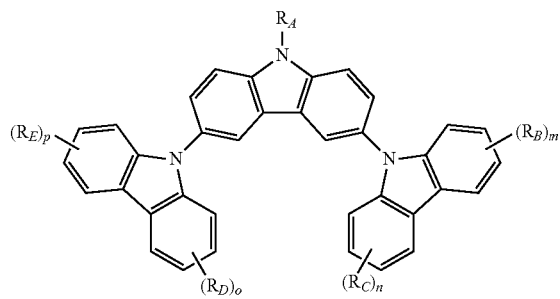

Formula (I)

wherein;

$R_A$ is a substituent comprising a substituted or unsubstituted cyclo- or polycycloalkyl group wherein the ring system comprises three to twenty carbon atoms or an aralkyl group having an overall number of nine to twenty carbon atoms, $R_B$, $R_C$, $R_D$ and $R_E$ are any substituent other than a substituted or unsubstituted aniline, and m, o, p and q are same or different at each occurrence and represent an integer from 0 to 4.

The triscarbazole compounds of the present invention can be used in various applications, including in light emitting diodes, photovoltaic cells or organic semiconductor devices. For example, those compounds can act as an efficient host material for phosphorescent emitters in light emitting diodes.

The present invention also provides a device, preferably a light emitting device comprising triscarbazole compounds in accordance with the present invention as well as a metal (such as Ir) complex.

BRIEF DESCRIPTION OF DRAWINGS

FIG. 3 shows layer configuration in OLED used in the evaluation of cycloalkyl substituted triscarbazole as host in an OLED containing a blue phosphorescent emitter.

DESCRIPTION OF EMBODIMENTS

Figure 1:
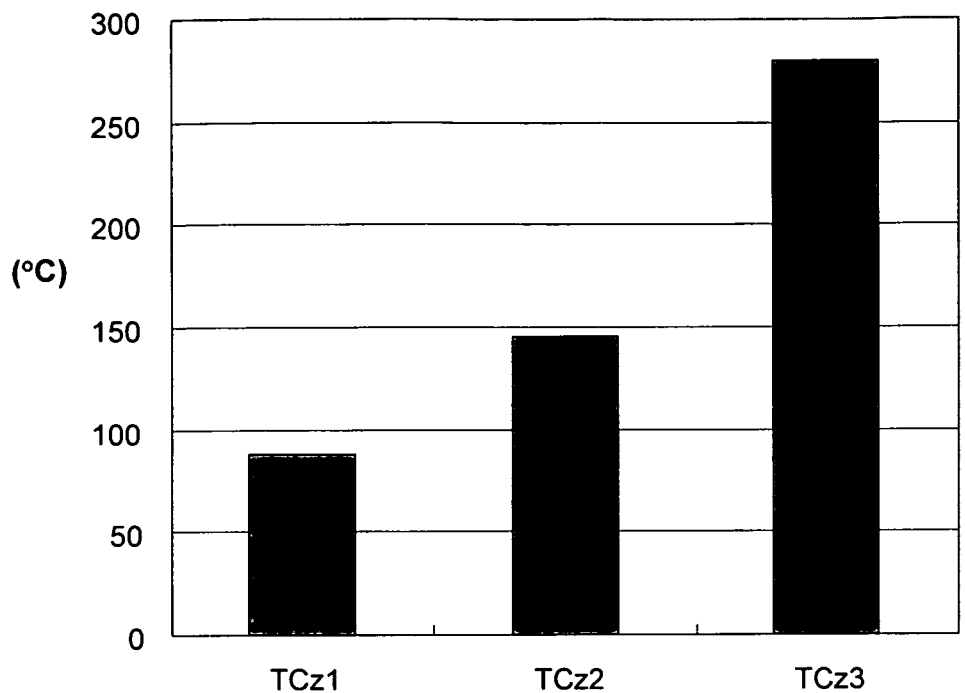
FIG. 1 shows glass transition temperatures of several triscarbazoles.

Molecular geometry plays a crucial role in the glass-forming ability of molecular systems. Common glass-forming topologies include branched or star shapes, spiro links, cycles, tetrahedral and twin molecular structures. When designing amorphous stable materials, structural features that increase Tg in addition to reducing crystal growth rate must be incorporated. Structural features that decrease free volume and restrict rotation about any molecular axis are expected to raise Tg. Inclusion of rigid and bulky groups such as tert-butyl, biphenyl and fluorene moieties increases Tg by hindering translational, rotational and vibrational motions of the molecule.

Guidelines for the molecular design of amorphous materials are provided in Shirota et al., "Charge carrier transporting molecular materials and their applications in devices," 107: 953-1010 (2007). It is described in the literature that incorporation of bulky and heavy substituents and enlargement of molecular size can lead to higher Tg. However, introduction of a branched alkyl chain on triscarbazoles (e.g., 2-ethylhexyl triscarbazole as represented by Formula (II) (hereafter, TCz1)) leads to a low glass transition temperature (Tg) and makes the material difficult to sublimate.

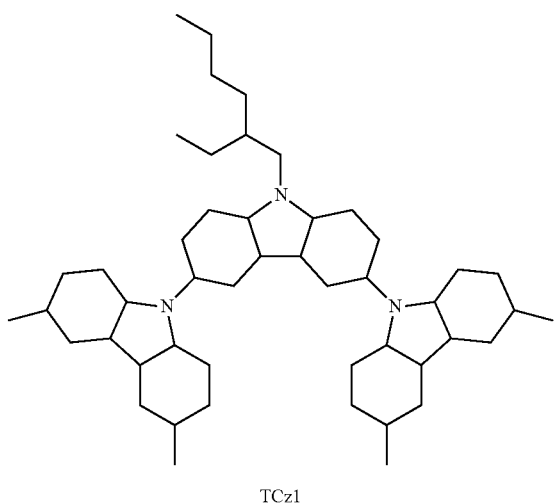

Formula (II)

TCz1

Thus, the present invention provides a host material, which comprises the compound of Formula (I):

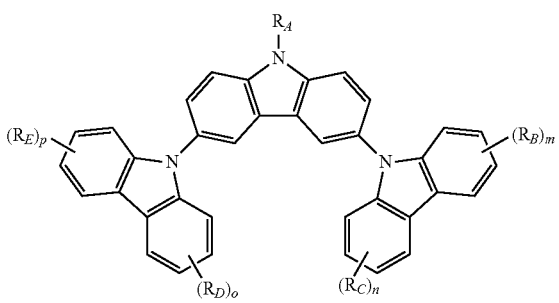

Formula (I)

wherein;

$R_A$ is a substituent comprising a substituted or unsubstituted cyclo- or polycycloalkyl group wherein the ring system comprises three to twenty carbon atoms or an aralkyl group having an overall number of nine to twenty carbon atoms, $R_B$, $R_C$, $R_D$ and $R_E$ are any substituent other than a substituted or unsubstituted aniline, and m, o, p and q are same or different at each occurrence and represent an integer from 0 to 4.

Cyclo- or polycycloalkyl substituents having three to twenty carbon atom, preferably five to twelve carbon atoms in the ring system, more preferably 6 to 12 carbon atoms and cyclopentyl are generally preferred over aralkyl substituents as defined above.

In some specific embodiments, $R_A$ is a cyclo- or polycycloalkyl substituent having five to twelve carbon atoms since such groups can lead to higher Tg or an aralkyl substituent having nine to fifteen carbon atoms (the number of carbon atoms in case of aralkyl substituents denoting the total number of carbon atoms in the substituent and not the number of carbon atoms in the aromatic ring system, e.g. 3,5-di.-t.-butylbenzyl having fifteen carbon atoms). In a preferred embodiment, $R_A$ is selected from the group consisting of cyclohexyl, cyclopentyl, adamantyl, quinuclidinyl, bornanyl, norbornanyl, bornenyl, 3,5-di-t-butylbenzyl and norbornenyl. In a more preferred embodiment, $R_A$ is selected from methylcyclohexyl or methyladamantyl. In the most preferred embodiment, $R_A$ is selected from methyladamantyl.

In some embodiments of the present invention, the other substituents $R_B$, $R_C$, $R_D$ and $R_E$ are hydrogen.

In a specific embodiment of the present invention, the following compound represented by Formulae (III) (hereafter, TCz2) or (IV) (hereafter, TCz3), and (V) (hereafter, TCzB1) are included.

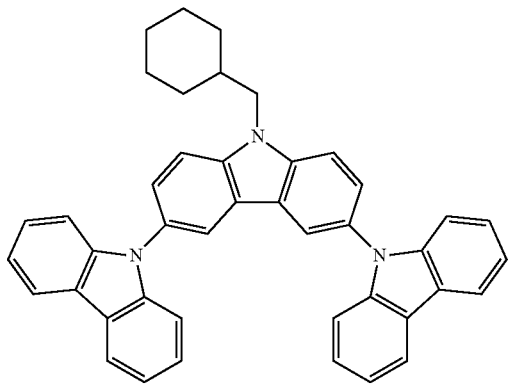

TCz2

Formula (IV)

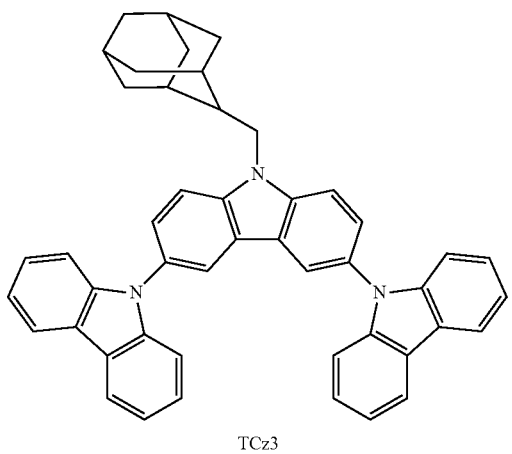

TCz3

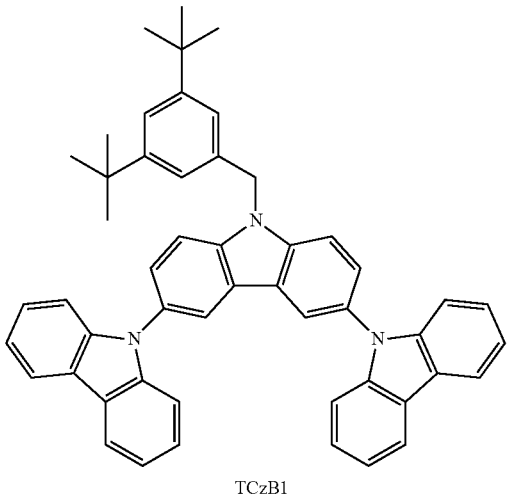

Formula (V)

TCzB1

The inventors of the present invention discovered that the glass transition temperatures of TCz2 and TCz3 are 145° C. and than 280° C., respectively, compared to 88° C. for TCz1. As such, sublimation yields also increase from 24% for TCz1 to 90% for TCz2 while the performances of devices are maintained.

The triscarbazole-based compounds having cyclo- or polycycloalkyl or aralkyl substituents in accordance with the present invention are frequently soluble in organic solvents such as toluene in concentrations exceeding 1 wt %. Thus, they can be applied in large-scale production of organic light emitting diodes since such solubilities allow solvent-processing techniques such as spin-coating, (ink-jet) printing processes, high concentration demanding printing processes (roll to roll, flexography, etc), etc., while maintaining the other necessary properties of OLED devices.

The synthesis of the triscarbazole compounds in accordance with the present invention can be accomplished by any known method. Generally, according to the embodiments of the present invention, the compounds of formula (I) can be prepared by the following reaction scheme via an appropriate reaction pathway, such as an Ullmann coupling reaction of a dihalogenated carbazole compounds with the corresponding carbazole derivatives.

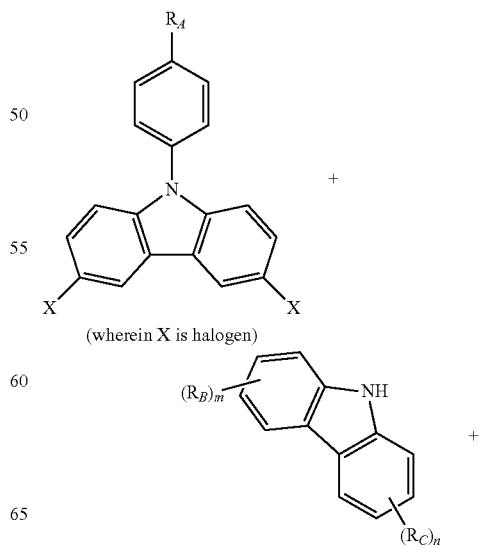

(wherein X is halogen)

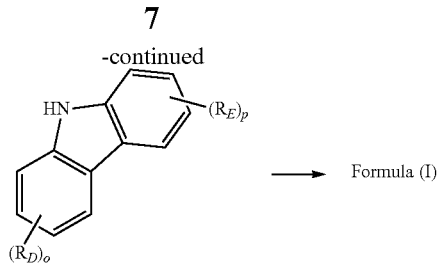

Formula (I)

In some embodiments where the Ullmann coupling reaction is used, copper/18-crown-6 is generally used as a catalyst and potassium carbonate as a base. The details about the Ullmann coupling reaction are described in many references in the art, e.g., Berichte der deutschen chemischen Gesellschaft. 1906, 39(2), 1691-1692 and in Hameurlaine et al. cited above.

The present invention is also directed to an organic device comprising the compounds according to the present invention.

Another aspect of the present invention relates to an organic device comprising at least one emissive layer containing a dopant and a host material comprising the compounds according to the present invention.

Suitable guest emissive (dopant) materials can be selected from those known in the art and hereafter developed including, without limitation, tris(2-phenylquinoline) iridium (III) complexes, which exhibit a phosphorescent emission in the orange region of the spectrum or Bis(4,6-difluorophenylpyridinato-N,C2)picolinato iridium which emits in the blue region of the spectrum. In specific embodiments, the guest exhibits a phosphorescent emission in the pure blue region of the spectrum.

If the emissive material is used as a dopant in a host layer comprising the compound of the present invention, then it is generally used in an amount of at least 1 wt %, specifically at least 3 wt %, and more specifically at least 5 wt %, with respect to the total weight of the host and the dopant. Further, it is generally used in an amount of at most 25 wt %, specifically at most 20 wt %, and more specifically at most 15 wt %.

The present invention is also directed to an organic light emitting device (OLED) comprising an emissive layer, wherein the emissive layer comprises the host material described above. The OLED also comprises an emissive material (where the light emitting material is present as a dopant), wherein the emissive material is adapted to emits light when voltage is applied across the device.

The OLED generally comprises:
a glass substrate;
a generally transparent anode such as an indium-tin oxide (ITO) anode;
(optionally) a hole injection layer (HIL);
a hole transporting layer (HTL);
an emissive layer (EML);
an electron transporting layer (ETL);
(optionally) a electron injection layer (EIL); and
a generally metallic cathode such as an Al layer.

As for the injection of holes, a hole injection layer (HIL) may be present between the anode and the hole transporting layer. As for the injection of electrons, an electron injection layer (EIL) may be present between the cathode and the electron transporting layer. A hole transporting layer may be present between the HIL and the emissive layer to conduct holes to the emissive layer. An electron blocking layer (EBL) may also be present between the emissive layer and the hole transporting layer. An electron transport layer may be present on the other side of the emissive layer to conduct electrons from the cathode over the electron injection layer to the emissive layer. A hole blocking layer (HBL) may also be present between the emissive layer and the electron transporting layer.

The emissive layer is formed with a host material comprising the compound of the present invention wherein the light emitting material is dispersed as a guest. Heavy metal complexes (e.g., Ir or Pt complexes) may be dispersed into host material comprising the compound of the present invention as a dopant for achieving electrophosphorescence.

The emissive layer may further comprise an electron-transporting material selected from the group consisting of metal quinoxolates (e.g., aluminium quinolate ($Alq_3$), bis-(2-methyl-8-quinolinolate)-4-(phenylphenolato)aluminium (BAblq), lithium quinolate (Liq)), oxadiazoles (e.g., tetrakis (4-(5-(3,5-di-tert-butylphenyl)-2-oxadiazolyl)phenyl)methane) and triazoles.

The electron transport layer is used to transport electrons into the emissive layer comprising the light emitting material and the host material. The electron transporting material may be an electron-transporting matrix selected from the group consisting of heteroaromatics, metal quinoxolates (e.g., $Alq_3$, BAblq and Liq), oxadiazoles, (e.g. 1,3-Bis[5-(4-tert-butylphenyl)-1,3,4-oxadiazole-2-yl]benzene or OXD-7,2-(4-Biphenylyl)-5-(4-tert-butylphenyl)-1,3,4-oxadiazole or PBD), triazoles (e.g. 3-(4-Biphenylyl)-4-phenyl-5-tert-butylphenyl-1,2,4-triazole or TAZ), substituted phenanthroline (e.g. 2,9-Dimethyl-4,7-diphenyl-1,10-phenanthroline or BCP, 4,7-Diphenyl-1,10-phenanthroline or BPhen), substituted benzimidazoles (e.g. 2,2',2"-(1,3,5-Benzinetriyl)-tris (1-phenyl-1-H-benzimidazole) or TBPI), borane compounds (e.g. tris[3-(3-pyridyl)-mesityl]borane or 3TPYMB) or substituted ketones (e.g. di(9,9'-spirobifluoren-2-yl) ketone or SBFK).

A suitable example of the material for the electron transport layer, without limitation, is 4,7-diphenyl-1,10-phenanthroline (Bphen) which has the following formula:

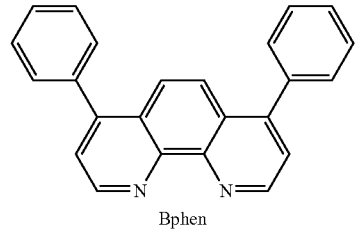 [SMILES: c1ccc(-c2ccnc3c2ccc2c(-c4ccccc4)ccnc23)cc1]

Bphen

The hole transport layer is used to transport holes into the emissive layer comprising the light emitting material and the host material. A suitable example of the hole transporting material, without limitation, is 4,4'-bis[N-(1-naphthyl)-N-phenylamino]biphenyl ["α-NPD"] which has the following formula:

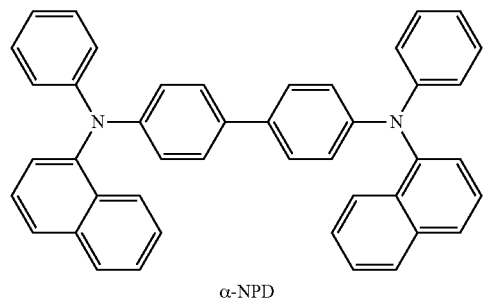 [SMILES: c1ccc(N(c2ccc(-c3ccc(N(c4ccccc4)c4cccc5ccccc45)cc3)cc2)c2cccc3ccccc23)cc1]

α-NPD

The use of the exciton blocking layer ("barrier layer") to confine excitons within the luminescent layer ("luminescent zone") is advantageous. the exciton blocking layer may be placed between the emissive layer and the electron transport layer. A suitable example of exciton transporting material is, without limitation, Bis-(2-methyl-8-quinolinolate)-4-(phenylphenolato)aluminium (BAlq):

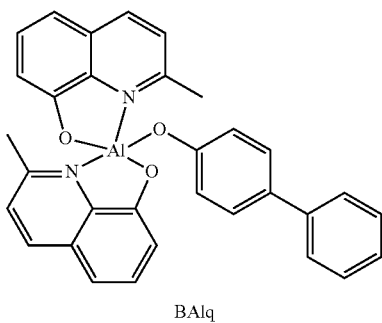

BAlq

The present invention also relates to a use of the compounds according to the present invention in light emitting diodes, photovoltaic cells or organic semiconductor devices.

EXAMPLES

Hereinafter, the present invention will be explained in detail with reference to examples and comparative examples. These examples, however, should not in any sense be interpreted as limiting the scope of the present invention. Further, units are expressed by weight unless otherwise described.

Comparative Example 1

Synthesis of Tricarbazole Compound of Formula (II)

The synthesis of TCz1 is described in Tsai et al., "3-(9-carbazolyl)carbazoles and 3,6-di(9-carbazolyl)carbazoles as effective host materials for efficient blue organic electrophosphorescence," *Adv. Mater.*, 19: 862-866 (2007).

Example 1

Synthesis of Tricarbazole Compound of Formula (III) (TCz2)

A. 3,6-dibromo-N-(cyclohexylmethyl)carbazole—BRCZ2

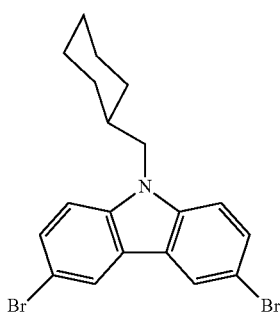 [SMILES: Brc1ccc2c(c1)c1cc(Br)ccc1n2CC1CCCCC1]

To a solution of 6.89 g (0.123 mol, 4.0 eq) of KOH in 100 ml of DMF stirred at room temperature were added 10.0 g (0.0308 mol, 1.0 eq) of solid 3,6-dibromocarbazole, followed, after one hour of stirring, by 6.54 g (0.0369 mol, 1.2 eq) of bromomethyl cyclohexane. The reaction was stirred for 16 h before the addition of 100 mL of half saturated aqueous $NaHCO_3$ solution. The mixture was then extracted with 2×50 ml of dichloromethane and the combined organic layers were dried over $MgSO_4$ and concentrated. The crude light brown solid was then purified by precipitation in $CHCl_3$/ethanol to afford 9.05 g (0.0215 mol, 70%) of BrCz2 as a white solid 96% NMR pure.

B. N-(cyclohexylmethyl)-3,6-bis(carbazol-9-yl)-carbazole—TCz2

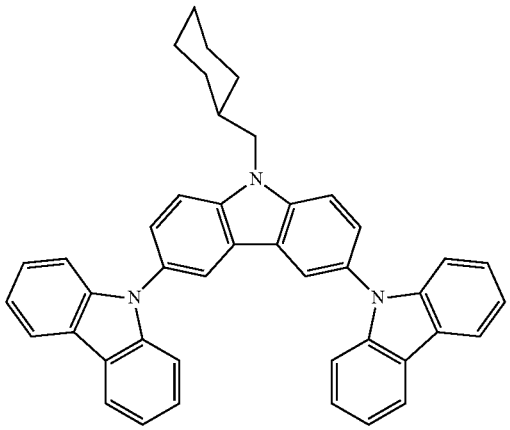 [SMILES: c1ccc2c(c1)c1ccccc1n2-c1ccc2c(c1)c1cc(-n3c4ccccc4c4ccccc43)ccc1n2CC1CCCCC1]

8.50 g (0.0202 mol, 1.0 eq) of BrCz2, 8.44 g (0.050 mol, 2.5 eq) of carbazole, 5.82 g (0.061 mol, 3.0 eq) of sodium tert. butoxylate, $^tBuONa$, 462 mg (0.500 mmol, 2.5 mol %) of $Pd_2(dba)_3$ and 817 mg (4.04 mmol, 20 mol %) of tris(tert-butyl) phosphine were stirred in 150 ml of dry toluene under $N_2$ atmosphere at reflux for 16 h. The reaction was cooled down to room temperature and the mixture was filtered through a path of Celite which was further rinsed by toluene. The filtrate was evaporated under vacuum to give an yellow-brown oil which is further purified by precipitation in $CHCl_3$/ethanol to afford 6.56 g (0.011 mol, 54%) of TCz2 as a white solid with 96% purity determined by NMR.

Example 2

Synthesis of Tricarbazole Compound of Formula (IV) (TCz3)

A. N-(3-methyladamantyl)carbazole—CZ3

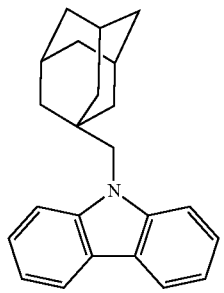 [SMILES: c1ccc2c(c1)c1ccccc1n2CC12CC3CC(CC(C3)C1)C2]

To a suspension of 1.24 g (0.0516 mol, 1.3 eq) of sodium hydride NaH in 100 ml of DMF stirred at room temperature were added 6.63 g (0.0397 mol, 1.0 eq) of solid carbazole. The mixture was heated at 80° C. for 8 h prior to the addition of 10.0 g (0.0436 mol, 1.1 eq) of 3-bromomethyl adamantane. The reaction was stirred for 14 h at 80° C. before and thereafter 100 ml of half saturated aqueous NaHCO$_3$ solution was added. The mixture is then extracted by 2×100 ml of chloroform and the combined organic layers are dried over MgSO$_4$ and concentrated. The crude pale yellow oil is then purified by flash chromatography (silica, hexanes/DCM) to afford 5.80 g (0.0184 mol, 46%) of Cz3 as a white solid with purity of 92% determined by NMR.

B. N-(3-methyladamantyl)-3,6-diiodocarbazole—ICZ3

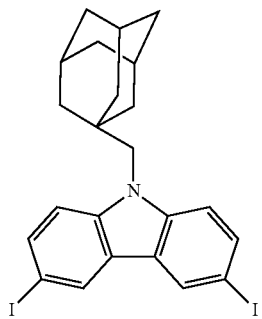 [SMILES: Ic1ccc2c(c1)c1cc(I)ccc1n2CC12CC3CC(CC(C3)C1)C2]

5.8 g (0.0184 mol, 1.0 eq) of Cz3 were dissolved in 150 ml of refluxing acetic acid. This solution was then cooled down at 100° C. and subsequently 4.03 g (0.0243 mol, 1.32 eq) of potassium iodide (KI) and 3.07 g (0.0143 mol, 0.78 eq) of potassium iodate (KIO$_3$) were added. After one hour under stirring, the mixture was poured into 300 ml of iced water and extracted with 3×100 ml of chloroform. The combined organic layers were then washed with a 5% Na$_2$S$_2$O$_3$ aqueous solution until turning clear and then with 200 ml of water. This solution was dried over MgSO$_4$ and concentrated under vacuum to afford a pale yellow crude product further purified by flash chromatography (silica, hexanes/DCM) to give 6.16 g (0.0109 mol, 59%) of a white solid with a purity of 92% determined by NMR. Despite the medium purity of this intermediate, it was used directly in the next step.

C. N-(3-methyladamantyl)-3,6-bis(carbazol-9-yl)-carbazole—TCz3

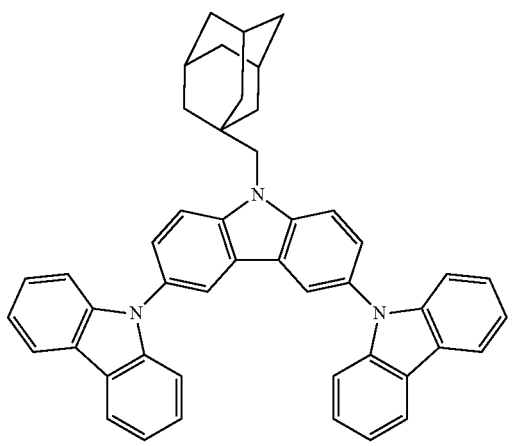 [SMILES: c1ccc2c(c1)c1ccccc1n2-c1ccc2c(c1)c1cc(-n3c4ccccc4c4ccccc43)ccc1n2CC12CC3CC(CC(C3)C1)C2]

5.49 g (0.0097 mol, 1.0 eq) of ICz3, 3.72 g (0.0223 mol, 2.3 eq) of carbazole, 16.1 g (0.117 mol, 12.0 eq) of K$_2$CO$_3$, 17.2 g (0.271 mmol, 28 eq) of Cu powder and 256 mg (0.0010 mol, 10 mol %) of 18-crown-6 were stirred in 250 ml of 1,2-dichlorobenzene at 178° C. under N$_2$ for 24 h. The reaction was cooled down to room temperature and the mixture was filtered through a path of Celite which was further rinsed by toluene. The filtrate was evaporated under vacuum to give a light brown oil which was further purified by precipitation in CHCl$_3$/ethanol to afford 4.62 g (0.00715 mol, 74%) of TCz3 as a white solid with a purity of 92% determined by NMR.

Example 3

Characterization of Triscarbazole Compounds of the Present Invention

HOMO-LUMO Measurements

The HOMO and LUMO values are estimated from cyclic voltammetry. The HOMO and LUMO values are respectively obtained from the 1$^{st}$ oxidation potential wave measured in dichloromethane and the 1$^{st}$ reduction potential measured in tetrahydrofurane.

Voltammetric measurements were performed using first a Metrohm VA Tracer Analyser 746 coupled with a computer-controlled AutoLab PGSTAT128N electrochemical workstation coupled with a 663 VA Stand measure unit.

Cyclic voltammograms were recorded under inert atmosphere (argon or nitrogen) in anhydrous dichloromethane or anhydrous tetrahydrofurane using 0.1 M tetrabutylammonium hexafluorophosphate as supporting electrolyte. The working electrode was a glassy carbon disk and the counter electrode a platinum wire. A silver/silver chloride electrode filled with a methanolic saturated KCl solution or a platinum wire pseudo-reference was used as reference electrode. The host solutions (0.5-1 mM) were degassed with argon before measurement.

Some of the characteristics of some of cyclo- or polycycloalkyl or aralkyl-substituted triscarbazoles of the present invention are shown in Table 1. All of the triscarbazoles shown in Table 1 are soluble in toluene to more than 1% by weight.

TABLE 1

| | Tg, ° C. | HOMO, eV | LUMO, eV | Sublimation yield, % |
|---|---|---|---|---|
| Comp Example (TCz1) | 88 | −5.46 | −1.62 | 24 |
| Example 1 (TCz2) | 145 | −5.45 | −1.69 | 90 |
| Example 2 (TCz3) | >280 | — | — | 82 |

FIG. 1 shows glass transition temperatures of several triscarbazoles. Glass transition temperatures of TCz1, TCz2 and TCz3 are 88, 145 and 280° C., respectively. There is 192° C. increase in Tg going from TCz1 to TCz3. These results are obtained due to the incorporation of the specific bulky and heavy substituents R$_4$ comprising ring systems into triscarbazole compounds, whereas TCz1 despite also having a bulky substituent but lacking a ring system shows a much lower Tg. As such, molecular size is enlarged. Molecular geometry plays an important role in the glass-forming ability of molecular systems, as mentioned above. The present invention shows that the inclusion of specific rigid and bulky groups such as methylcyclohexyl or methyladamantyl significantly increases Tg by hindering translational, rotational and vibrational motions of the molecule. Increase of Tg makes the material easy to sublimate. This is the reason for high Tg and sublimation yield of TCz2 and TCz3.

Example 4

Light Emitting Properties of OLED from Triscarbazole Compounds

Figure 2:
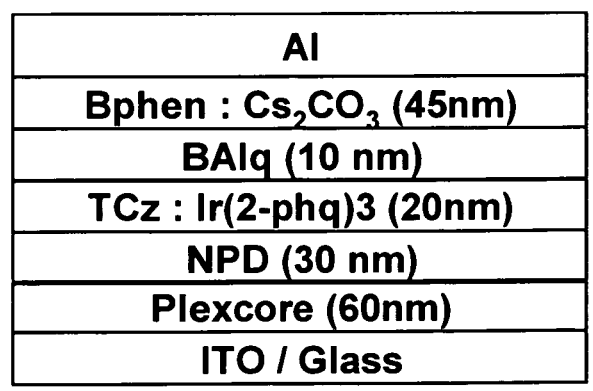
FIG. 2 shows layer configurations in OLED used in the evaluation of cycloalkyl substituted triscarbazole derivatives as host in an OLED device made by vacuum process and containing an orange phosphorescent emitter

A general structure as shown in FIG. 2 was used to fabricate an OLED having an emissive layer (EML) containing compounds TCz2 and TCz3 in accordance with the present invention.

A reference OLED containing NPD as a host was fabricated to benchmark the performance of the triscarbazole based compounds of the present invention. Keeping the OLED structure identical, devices based on TCz2 and TCz3 were fabricated to compare device performance with those of NPD. Apart from the compound of the present invention, the EML comprises tris(2-phenylquinoline)iridium(III) (Ir(2-phq)$_3$) as a dopant.

Light emitting devices were fabricated as below: a Plexcore OC AQ-1100 supplied from Plextronics was deposited by spin coating on indium tin oxide (ITO) coated glass substrate to a thickness of 60 nm. The obtained film was dried on a hot plate at 200° C. for 10 min. The NPD and the emissive layer (host: Ir(2-phq)$_3$ formulation) were deposited by vacuum deposition to thicknesses of 30 nm and 20 nm, respectively. An 10 nm of barrier layer, namely, Bis-(2-methyl-8-quinolinolate)-4-(phenylphenolato)aluminium (BAblq), was deposited by vacuum deposition onto the EML. An 45 nm of 4,7-diphenyl-1,10-phenanthroline (BPhen):Cs$_2$CO$_3$ layer was co-evaporated onto the barrier layer. Finally, aluminum cathode layer was deposited by thermal evaporation.

Electronic and photometric characterizations were conducted using a Hamamatsu C9920-12 measurement system coupled to a Keithley 2400 source measure unit. All of the device fabrication and characterization steps after spin coating of the hole injection layer (HIL) were carried out in an inert atmosphere.

Table 2 shows efficiencies of devices comprising NPD (as reference), TCz2 and TCz3. For the similar operating voltages, work for operation decreased in Examples 1 and 2 compared to Comparative Example 2. As such, the luminescence and brightness of light increased while the CIE color coordinates (x, y) was maintained. This means that the efficiency of device increased, while the increasing value was almost twice in Example 2 compared to Comparative Example 2 (as shown in table 2). The efficiency of device comprising TCz3 is the best, while that comprising NPD is the worst. This result demonstrates that bulky cyclo- or polycycloalkyl or aralkyl group substituted TCz makes a material easier to sublimate. This enhances film morphology in a device which may lead to enhanced stability and increased lifetime.

TABLE 2

| Device | 1000 cd/m$^2$ | | | | | |
|---|---|---|---|---|---|---|
| | V | J | EQE | Lm/W | Cd/A | X | Y |
| NPD (Comparative Example 2) | 3.1 | 23.8 | 2.2 | 4.3 | 4.2 | 0.59 | 0.41 |
| Example 1 (TCz2) | 3.4 | 15.4 | 3.9 | 6.0 | 6.5 | 0.60 | 0.40 |
| Example 2 (TCz3) | 3.3 | 13.8 | 4.5 | 7.0 | 7.3 | 0.60 | 0.39 |

A general structure as shown in FIG. 3 was used to fabricate OLED devices having an emissive layer (EML) containing TCz2 of the present invention in various amounts.

Keeping the OLED structure identical, devices based on TCz2 were fabricated to compare performance with that based on TCz1. Apart from the host, the EML comprised an electron transporter (tetrakis(4-(5-(3,5-di-tert-butylphenyl)-2-oxadiazolyl)phenyl)methane (tBuOXD7)) to achieve charge balance and Bis(4,6-difluorophenylpyridinato-N,C2)picolinatoiridium (Firpic) as a blue phosphorescent emitter. The EML compositions of TCz2:tBuOXD7:Firpic were varied from 65:30:5 to 35:60:5, all ratios being weight ratios.

The EML composition of the reference OLED was TCz1:tBuOXD7:Firpic in 45:50:5 weight ratio. The details of preparation of tBuOXD7 are disclosed in European patent application 2 282 358.

Device fabrication was performed as follows: The ITO surface was cleaned with solvents in an ultrasonic bath then treated for 10 min with UV/ozone cleaner prior to fabrication. A 60 nm PEDOT:PSS (CH8000 from HC Stark) layer (HIL) was spin-coated onto the ITO coated glass substrate. The PEDOT:PSS layer was dried on a hot plate in a nitrogen atmosphere at 200° C. for 10 min. A 70 nm EML layer was spin-coated from 1.5% wt formulations in toluene. The EML was subsequently dried on a hot plate in a nitrogen atmosphere at 80° C. for 10 min. Then the ETL (3TPYMB, 30 nm, evap. rate 2 Å/s), Cs$_2$CO$_3$ (1 nm, evap. rate 0.1 Å/s) and the aluminum top metal contact (100 nm, evap. rate 2 Å/s) were evaporated in sequence using a Lesker Spectros system at a pressure of 2.0-5.0×10$^{-6}$ mbar.

Inventors evaluate the TCz2 of the present invention as host in spin-coated blue OLEDs. Table 3 shows efficiencies of devices comprising TCz1 (as reference) or TCz2, tBuOXD7 and Firpic with different ratios. For the similar operating voltages, the speed and intensity of light of devices comprising TCz2:tBuOXD7:Firpic mixtures having 55:40:5 and 45:50:5 ratios, respectively, were similar to those of a device comprising TCz1:tBuOXD7:Firpic mixture having 45:50:5 ratio, while the CIE color coordinates (x, y) are maintained. This means that the efficiencies of devices were also similar. Further, it demonstrates solution processing with performance as high as TCz1.

TABLE 3

| Device | 1000 cd/m$^2$ | | | | | |
|---|---|---|---|---|---|---|
| | V | EQE | Lm/W | Cd/A | x | Y |
| TCz2:tBuOXD7:Firpic 65:30:5 | 5.3 | 6.8 | 8.6 | 14.4 | 0.16 | 0.35 |
| TCz2:tBuOXD7:Firpic 55:40:5 | 5.2 | 8.5 | 10.9 | 18.1 | 0.16 | 0.35 |
| TCz2:tBuOXD7:Firpic 45:50:5 | 5.5 | 8.5 | 10.6 | 18.5 | 0.17 | 0.36 |
| TCz2:tBuOXD7:Firpic 35:60:5 | 5.9 | 7.8 | 9.1 | 16.9 | 0.17 | 0.36 |
| TCz1:tBuOXD7:Firpic 45:50:5 (Comparative Example 1) | 5.7 | 8.5 | 10.1 | 18.4 | 0.17 | 0.36 |

It will be apparent to those skilled in the art that various modifications and variations to the foregoing examples can be made within the scope of the claims.

The invention claimed is:

1. A compound of Formula (I):

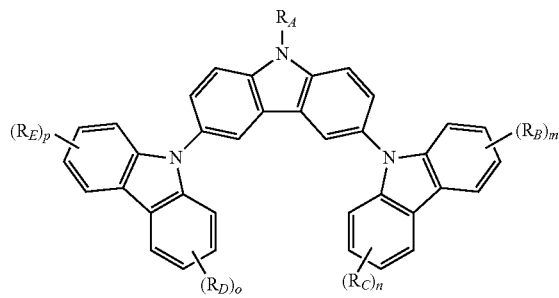

wherein;

$R_A$ is a substituent comprising a substituted or unsubstituted cyclo- or polycycloalkyl group wherein the ring system comprises three to twenty carbon atoms selected from the group consisting of cyclohexyl, cyclopentyl, adamantyl, bornanyl, norbornanyl and bornenyl, or an aralkyl group having an overall number of nine to twenty carbon atoms, $R_B$, $R_C$, $R_D$ and $R_E$ are hydrogen, and m, o, p and q are same or different at each occurrence and represent an integer from 0 to 4.

2. The compound of claim 1 wherein $R_A$ is a substituted or unsubstituted cyclo- or polycycloalkyl group wherein the ring system comprises three to twenty carbon atoms selected from the group consisting of cyclohexyl, cyclopentyl, adamantyl, bornanyl, norbornanyl and bornenyl.

3. The compound of claim 1, wherein $R_A$ is a substituent comprising a substituted or un substituted cyclo- or polycycloalkyl group having six to twelve carbon atoms in the ring system or an aralkyl group having an overall number of nine to fifteen carbon atoms.

4. The compound of claim 3 wherein $R_A$ is a substituent comprising a substituted or unsubstituted cyclo- or polycycloalkyl having group six to twelve carbon atoms in the ring system.

5. The compound of claim 3, wherein $R_A$ is methylcyclohexyl.

6. The compound of claim 3, wherein $R_A$ is methyladamantyl.

7. The compound of claim 3, wherein $R_A$ is 3,5-di-t-butylbenzyl.

8. The compound of claim 1, wherein the compound is represented by any one of Formulae (III) to (V)

Formula (III)

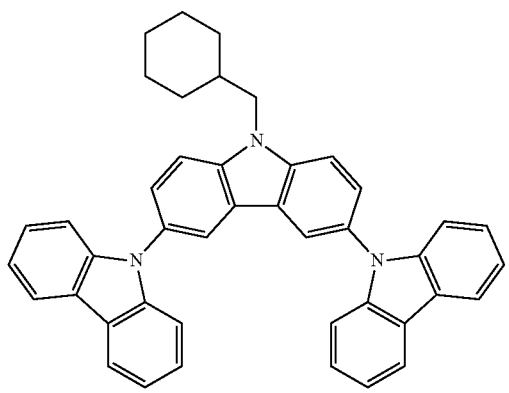

Formula (IV)

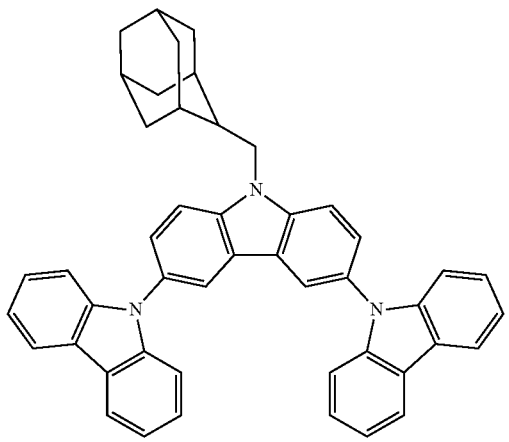

Formula (V)

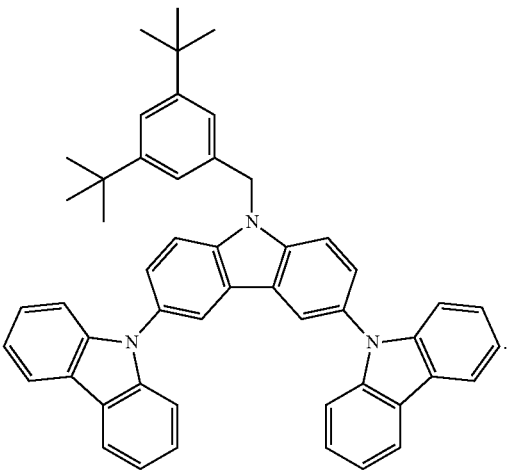

9. An organic device comprising the compounds according to claim 1.

10. An organic device wherein an emissive layer in the device comprises the compounds according to claim 1.

11. The device of claim 10, wherein the device is a light emitting device, a photovoltaic cell device, or an organic semiconductor device.

* * * * *